(12) United States Patent  (10) Patent No.: US 9,108,065 B2
Srivastava et al.  (45) Date of Patent: Aug. 18, 2015

(54) RF TRANSCEIVER HOPPING FOR COMMUNICATION WITH IMPLANTABLE MEDICAL DEVICE

(75) Inventors: Nishant Srivastava, Los Angeles, CA (US); Allan R. Schwartz, Thousand Oaks, CA (US); Curtis A. Knight, Santa Clara, CA (US)

(73) Assignee: PACESETTER, INC., Sylmar, CA (US)

( * ) Notice: Subject to any disclaimer, the term of this patent is extended or adjusted under 35 U.S.C. 154(b) by 865 days.

(21) Appl. No.: 13/246,575

(22) Filed: Sep. 27, 2011

(65) Prior Publication Data

US 2013/0079836 A1   Mar. 28, 2013

(51) Int. Cl.
  *A61N 1/08*   (2006.01)
  *A61N 1/372*   (2006.01)

(52) U.S. Cl.
  CPC ........ *A61N 1/37235* (2013.01); *A61N 1/37211* (2013.01); *A61N 1/37252* (2013.01)

(58) Field of Classification Search
  None
  See application file for complete search history.

(56) References Cited

U.S. PATENT DOCUMENTS

| 6,167,312 | A * | 12/2000 | Goedeke | 607/60 |
|---|---|---|---|---|
| 7,072,718 | B2 * | 7/2006 | Von Arx et al. | 607/60 |
| 7,672,731 | B2 | 3/2010 | Dublin et al. | |
| 2006/0195162 | A1 | 8/2006 | Arx et al. | |
| 2007/0032832 | A1 * | 2/2007 | Feher | 607/32 |
| 2008/0288024 | A1 | 11/2008 | Abrahamson et al. | |
| 2009/0132008 | A1 | 5/2009 | Snitting et al. | |
| 2010/0272151 | A1 | 10/2010 | Nandagopalan et al. | |
| 2010/0273436 | A1 | 10/2010 | Trachewsky et al. | |
| 2010/0273437 | A1 | 10/2010 | Nandagopalan et al. | |
| 2011/0038360 | A1 | 2/2011 | Ho | |

FOREIGN PATENT DOCUMENTS

WO   2006093766 A1   9/2006
WO   2006130060 A1   12/2006

* cited by examiner

*Primary Examiner* — Kennedy Schaetzle

(57) ABSTRACT

Dynamically switching between different external RF transceivers for communication with an implantable medical device maintains high communication quality in the face of interference, fading, detuning, or other adverse wireless communication conditions. Quality information associated with communications between an implantable medical device and different external devices is monitored to select one of these external devices to conduct subsequent communication with the implantable medical device. This monitoring is conducted on a repeated basis such that communication is switched to a different RF transceiver whenever such an RF transceiver is able to achieve a higher quality communication than the currently selected RF transceiver. In some embodiments, RF transceivers are deployed in different devices. For example, one or more RF transceivers may be deployed at a portable programmer (e.g., in the form of a computer tablet) and one or more other RF transceivers may be deployed at an associated base station.

27 Claims, 11 Drawing Sheets

US 9,108,065 B2

RF TRANSCEIVER HOPPING FOR COMMUNICATION WITH IMPLANTABLE MEDICAL DEVICE

TECHNICAL FIELD

This application relates generally to implantable medical device technology and more specifically, but not exclusively, to hopping between RF transceivers to communicate with an implantable medical device.

BACKGROUND

Implantable medical devices are employed in various applications. For example, an implantable cardiac device may perform one or more functions including sensing signals generated in a patient's heart, pacing the heart to maintain regular contractions, and providing defibrillation shocks to the heart. Similarly, an implantable stimulation device may be used to apply stimulation signals to a patient's muscular tissue, neurological system, or some other area of the patient's body.

In many cases, there is a need to communicate with an implantable medical device after it has been implanted in a patient. For example, an external monitoring device located in an operating room, a doctor's office, a clinic, a person's home, or some other suitable location may be used to retrieve information collected by and/or stored in the implanted medical device. In the case of an implanted cardiac device, such information may include sensed cardiac activity data that a treating physician may analyze to learn about the patient's health. Similarly, an external programming device (which typically includes monitoring capabilities as well) may be used by a treating physician to change the operating parameters of the implanted medical device. Such parameters include, for example, the timing or magnitude of stimulation pulses generated by the implanted medical device.

Typically, radiofrequency (RF) telemetry is employed for communication between an external device and an implanted medical device. In such a case, the external device and the implanted medical device each Include an RF transceiver that transmits and receives RF signals (e.g., via a designated medical band).

In practice, communication problems may be encountered when an external device and implanted medical device attempt to communicate with one another. For example, a transmitting device typically transmits RF signals at low power levels to reduce the possibility that these RF transmissions will interfere with other nearby RF devices (e.g., an external device and/or an implanted medical device located in a nearby room). However, environmental conditions such as objects in the room and nearby noise sources may interfere with the reception of such low power RF signals. Consequently, under certain circumstances, a receiving device may not be able to accurately acquire the information sent via these RF signals. Thus, there is a need for improved techniques for communicating between an implantable medical device and an external device.

SUMMARY

A summary of several sample aspects of the disclosure follows. This summary is provided for the convenience of the reader and does not wholly define the breadth of the disclosure. For convenience, the term some aspects may be used herein to refer to a single aspect or multiple aspects of the disclosure.

The disclosure relates in some aspects to dynamically switching between different RF transceivers in an attempt to maintain the highest possible communication quality when communicating with an implantable medical device. Here, communication quality associated with each external device is monitored to select one of these external devices to conduct subsequent communication with the implantable medical device. This monitoring is conducted on a repeated basis such that communication is switched to a different RF transceiver whenever such an RF transceiver is able to achieve higher quality communication than the currently selected RF transceiver.

In some embodiments, RF transceivers are deployed in different devices. For example, one or more RF transceivers are deployed at a portable programmer (e.g., in the form of a computer tablet) and one or more other RF transceivers are deployed at a base station in some cases. Due to the different locations of these RF transceivers, it is likely that at least one of these RF transceivers will provide high quality communication with the implantable medical device at a given point in time. Accordingly, a hopping scheme as taught herein may be employed to determine, on an ongoing basis, an RF transceiver that currently provides the best implantable medical device communication.

In some embodiments, multiple RF transceivers are deployed in a single device. For example, two or more RF transceivers are deployed at a programmer in some cases. By placing these RF transceivers at different locations (e.g., with different antenna orientations), it is likely that at least one of these RF transceivers will provide high quality communication with the implantable medical device at a given point in time. Accordingly, a hopping scheme as taught herein also may be employed in these cases to maintain quality implantable medical device communication.

BRIEF DESCRIPTION OF THE DRAWINGS

These and other aspects of the disclosure will be more fully understood when considered with respect to the following detailed description, the appended claims, and the accompanying drawings, wherein:

Figure 1:
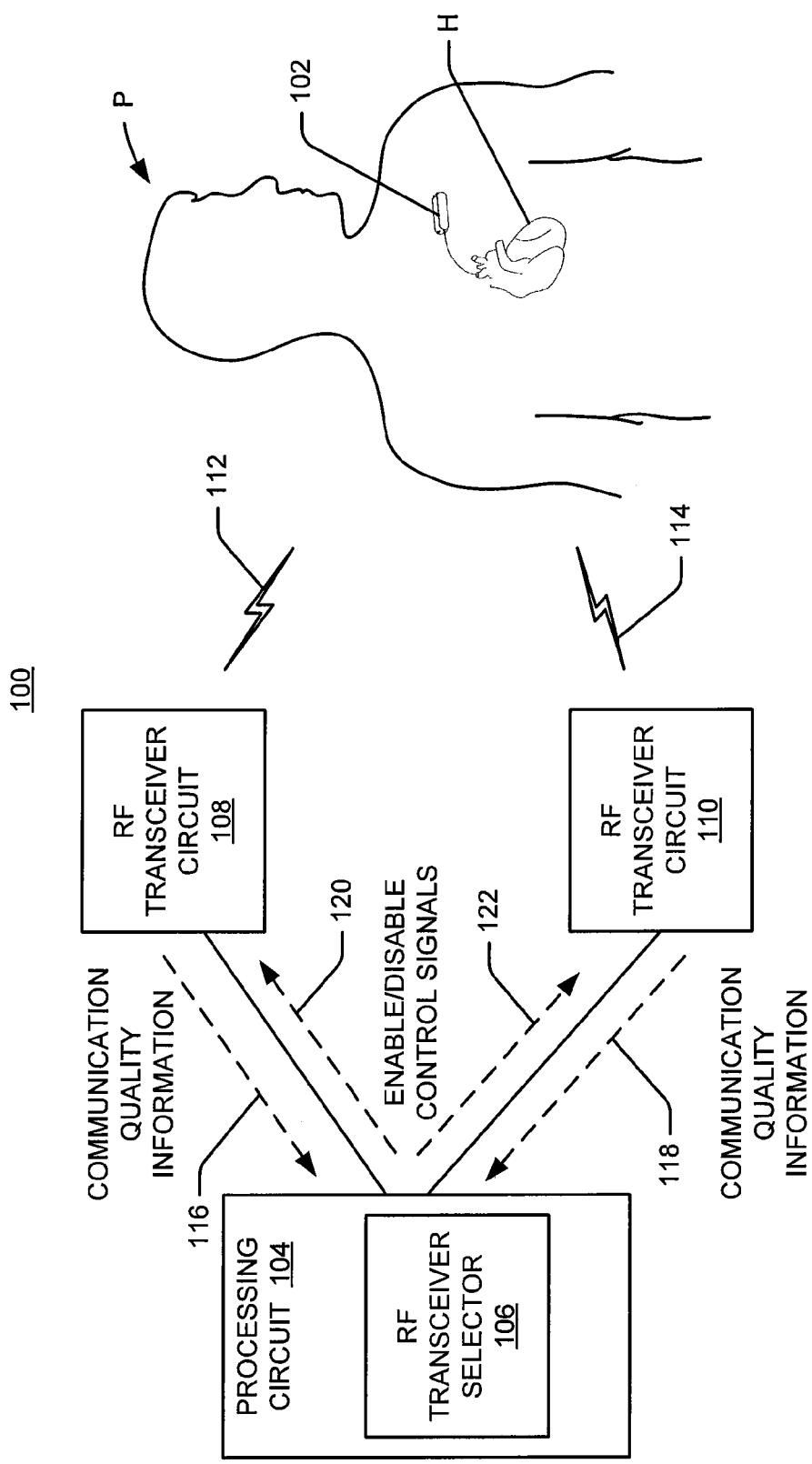
FIG. 1 is a simplified diagram of an embodiment of a communication system where one RF transceiver circuit of a set of RF transceiver circuits is selected to communicate with an implantable medical device.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 illustrates, in a simplified manner, an embodiment of a communication system 100 where multiple RF transceiver circuits are used for communicating with an implantable medical device 102. In particular, the RF transceiver circuit that currently provides the best communication quality at a given point in time is selected to communicate with the implantable medical device 102. For example, at some point in time, a currently selected RF transceiver circuit may experience fading, detuning, interference, or some other condition that adversely affects the communication between that RF transceiver circuit and the implantable medical device 102. In this case, if another RF transceiver circuit is able to provide better communication with the implantable medical device 102 at that point in time, the other RF transceiver circuit is selected for communication with the implantable medical device 102 in place of the previously selected RF transceiver circuit. This RF transceiver hopping scheme may be particularly advantageous since communication with implantable medical devices is conducted using a relatively low transmit power (e.g., 25 microwatts or less) and, hence, over a relatively small effective coverage range (e.g., on the order of 10 meters or less). Hence, such communication is particularly susceptible to degradation from interference, fading, and so on.

An RF transceiver circuit hopping scheme as taught herein may be employed to communicate with various types of implantable medical devices. In the embodiment of FIG. 1, the implantable medical device 102 is an implantable cardiac device that is implanted within a patient P. The implantable medical device 102 is connected to at least one implantable lead that is terminated within, on, or near the heart H of the patient P. A more detailed embodiment of such an implantable medical device is described below at FIGS. 10 and 11. In other embodiments, an implantable medical device may take the form of a neurological device, or some other type of device that is implanted within a patient.

In FIG. 1, a processing circuit 104 includes an RF transceiver selector 106 that selects either an RF transceiver circuit 108 or an RF transceiver circuit 110 for subsequent communication with the implantable medical device 102. As discussed in more detail below, other embodiments may employ a different number of RF transceiver circuits (e.g., 3, 4, or more). The RF transceiver circuit 108 and the RF transceiver circuit 110 are configured to communicate with the implantable medical device 102 via a suitable RF band as represented by the respective wireless symbols 112 and 114. For example, in some embodiments these components support a medical RF band such as a medical implant communication service (MICS) band or an industrial, scientific, and medical (ISM) band.

The RF transceiver selector 106 selects an RF transceiver circuit based on communication quality information associated with the communication between each RF transceiver circuit and the implantable medical device 102. As represented by the dashed line 116, the processing circuit 104 receives information indicative of the quality of communication between the RF transceiver circuit 108 and the implantable medical device 102. Similarly, as represented by the dashed line 118, the processing circuit 104 receives information indicative of the quality of communication between the RF transceiver circuit 110 and the implantable medical device 102.

The information provided by the RF transceiver circuits 108 and 110 takes different forms in different embodiments. In some cases, the information provided by the RF transceiver circuits 108 and 110 comprises data received by the RF transceiver circuits from the implantable medical device 102. In some cases, the information provided by the RF transceiver circuits 108 and 110 comprises a characterization of the RF signals received by the RF transceiver circuits 108 and 110 (e.g., received signal strength measurements). In some cases, the information provided by the RF transceiver circuits 108 and 110 comprises a characterization of the data received by the RF transceiver circuits 108 and 110 (e.g., an indication of a received data error rate).

The RF transceiver selector 106 uses the received information (e.g., directly or after processing of the received information) to determine an indication of the quality of the communication associated with each RF transceiver circuit. These quality indications take different forms in different embodiments. In some cases, this information comprises received signal strength information (e.g., a received signal strength indicator (RSSI)) corresponding to the RF signals received by a corresponding one of the radiofrequency transceiver circuits. In some cases, this information comprises telemetry signal strength information (e.g., a telemetry signal strength indicator (TSI)). In some cases, this information comprises signal-to-noise ratio (SNR) information. In some cases, this information comprises cyclic redundancy check (CRC) information corresponding to information embedded in the RF signals received by a corresponding one of the radiofrequency transceiver circuits. In some cases, this information comprises error correcting code (ECC) information corresponding to information embedded in the RF signals received by a corresponding one of the radiofrequency transceiver circuits. In some cases, this information comprises throughput information corresponding to information embedded in the RF signals received by a corresponding one of the radiofrequency transceiver circuits. In some cases, two or more different types of information (e.g., signal strength and CRC) are used to provide the quality indications.

Based on the quality indications, the RF transceiver selector 106 identifies the RF transceiver circuit that provides the best communication with the implantable medical device 102. For example, the RF transceiver circuit associated with the lowest error rate, the strongest signal strength, the highest throughput, or some other factor or combination of factors may be identified here. As represented by the dashed lines 120 and 122, the processing circuit 104 sends controls signals to the RF transceiver circuits to enable the selected RF transceiver circuit for subsequent communication with the implantable medical device 102 and disable each non-selected RF transceiver circuit for subsequent communication with the implantable medical device 102. As discussed in more detail below, a dynamic selection process (e.g., a hopping scheme) is generally employed, whereby the communication quality information is monitored over time and a different RF transceiver circuit is selected in place of the currently selected RF transceiver circuit whenever better communication with the implantable medical device 102 can be achieved by such a switch.

External components such as the RF transceiver circuits 108 and 110 of FIG. 1 are deployed in different devices in different implementations. In some implementations, two or more of the RF transceiver circuits are deployed in the same device (e.g., in a programmer). In some implementations, RF transceiver circuits are deployed in different devices (e.g., at a base station and at a portable programmer). Several examples of these different configurations are described in more detail below.

Figure 2:
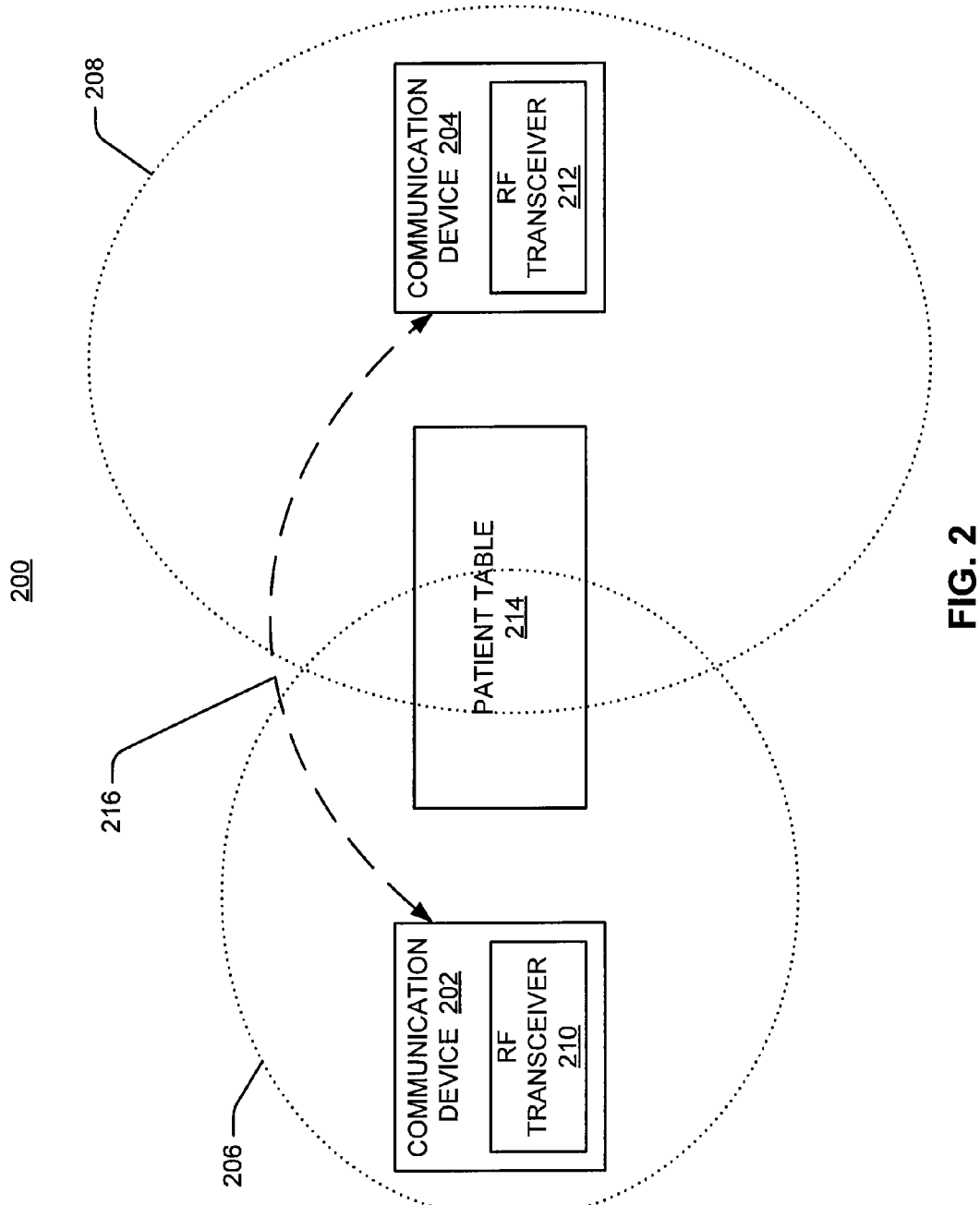
FIG. 2 is a simplified diagram of an embodiment of a communication system illustrating sample RF coverage for different RF transceivers.

FIG. 2 illustrates an embodiment of a system 200 where RF transceiver circuits (hereafter referred to simply as RF transceivers) are advantageously deployed in different communication devices 202 and 202. In this case, the communication devices 202 and 204 may be located at different locations in a room thereby providing a larger overall RF coverage area and/or providing improved communication performance in the event there are obstructions or interference conditions in the room.

The dashed circles 206 and 208 of FIG. 2 illustrate, in a simplified manner, how the communication devices 202 and 204 provide a large effective coverage area through the use of the hopping technique taught herein. When the RF transceiver 210 is selected to communicate with an implantable medical device (not shown in FIG. 2), RF coverage is provided in the area represented by the dashed circle 206. Conversely, when the RF transceiver 212 is selected to communicate with the implantable medical device, RF coverage is provided in the area represented by the dashed circle 208. Thus, irrespective of where the implantable medical device may be located at a given point in time (e.g., the patient may be on the patient table 214 or elsewhere in the room), the implantable medical device will likely be within the coverage of at least one of the RF transceivers 210 and 212.

In some implementations, the communication devices 202 and 204 provide different forms of RF coverage. For example, the RF coverages may have different signal patterns (e.g., the corresponding antenna radiation patterns may have different coverage areas and/or may have different signal quality at different distances), different gain characteristics, and so on.

In the example of FIG. 2, the RF transceiver 212 provides a larger coverage area. In some cases, this is accomplished by employing different antennas that have higher gains (e.g., larger antennas and/or different types of antennas) and/or by using a higher transmit power. Such a configuration may be employed, for example, in a case where the communication device 202 is a portable device such as a tablet computing system (e.g., the device is relatively small and has battery power constraints) and where the communication device 204 is a less portable device such as a base station (e.g., the device is larger and operates on AC power).

The hopping scheme taught herein may be employed where the communication devices 202 and 204 are deployed at different locations or even when they are deployed at the same location. As an example of the former scenario, in the event there is a temporary obstruction (e.g., a person) or a permanent obstruction (e.g., a piece of furniture or equipment) between one communication device and the implantable medical device, the other communication device may be able to provide better communication with the implantable medical device. As an example of the latter scenario, the orientation of the antennas (and/or different types of antennas) used by one of the communication devices (e.g., a portable device) may result in that communication device providing better quality communication with the implantable medical device than the other communication device.

In embodiments where the RF transceivers are deployed in different communication devices, hopping between the RF transceivers is achieved by means of a communication channel between the communication devices. For example, in FIG. 2, one of the communication devices 202 and 204 will include a processing circuit (not shown) that communicates with an on-device RF transceiver via an internal connection and with an off-device RF transceiver via RF signaling as represented by the dashed line 216. Several examples of such inter-device communication are described in more detail below.

Figure 3:
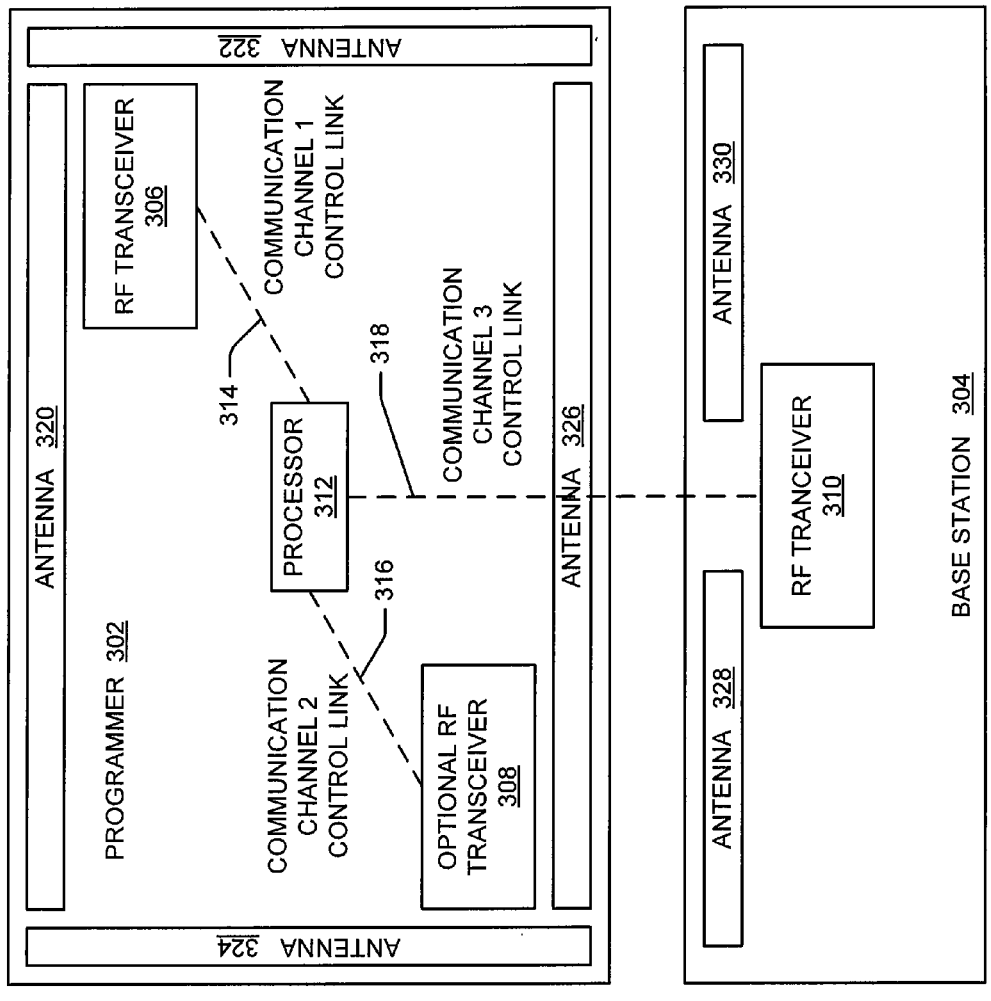
FIG. 3 is a simplified block diagram of an embodiment of a communication system where RF transceivers associated with different antenna orientations are deployed in different devices.

FIG. 3 illustrates an embodiment of a system 300 that employs hopping between RF transceivers that are deployed in a programmer 302 and an associated base station 304. For example, the programmer 302 may take the form of a tablet computing system configured with appropriate software such that a physician, a clinician, or other operator uses the programmer 302 to program and upload information from an implantable medical device (not shown). The base station 304 typically includes components (not shown) that provide communication network (e.g., the Internet) connectivity functionality, surface electrocardiogram (ECG) functionality, programmer battery charging functionality, and other functionality.

Under certain conditions, the communication between a given RF transceiver and an implantable medical device in the system 300 may be subject to one or more of signal fading, detuning, changes in relative polarization of transmit and receive antennas, or noise. These factors may result in signal degradation or even loss of signal in some cases. As mentioned above, this susceptibility to communication degradation is due, in part, to the low transmit power levels and limited range generally employed for communication with an implantable medical device.

In accordance with the teachings herein, the system 300 employs hopping between RF transceivers so that effective communication with the implantable medical device is maintained even if the communication between the implantable medical device and one of the RF transceivers degrades. Here, the programmer 302 includes an RF transceiver 306 (and optionally an RF transceiver 308), while the base station 304 includes an RF transceiver 310. The programmer 302 also includes a processor 312 (e.g., corresponding to the processing circuit 104 of FIG. 1) that controls the RF transceiver hopping by dynamically selecting the RF transceiver that communicates with the implantable medical device.

To facilitate this control function, the processor 312 maintains control links with each of the RF transceiver circuits. One control link 314 is established for controlling a communication channel 1 between the implantable medical device and the RF transceiver 306. Another control link 316 is established for controlling a communication channel 2 between the implantable medical device and the RF transceiver 308. Yet another control link 318 is established for controlling a communication channel 3 between the implantable medical device and the RF transceiver 310. As described at FIG. 4 below, the control link 318 between the programmer 302 and the base station 304 is typically implemented using a wireless link.

The processor 312 receives communication quality information as discussed herein from each of the RF transceivers 306, 308, and 310. Specifically, the RF transceiver 306 sends information indicative of the quality of communication channel 1 to the processor 312 via the control link 314. The RF transceiver 308 sends information indicative of the quality of communication channel 2 to the processor 312 via the control link 316. The RF transceiver 310 sends information indicative of the quality of communication channel 3 to the processor 312 via the control link 318.

The processor 312 uses the received communication quality information to select one of the RF transceivers 306, 308, and 310 for subsequent communication with the implantable medical device as discussed herein. For example, if the RF transceiver 306 is selected, the processor 312 sends a control message over the control link 314 that configures the RF transceiver 306 to communicate with the implantable medical device for subsequent operations. Conversely, the processor 312 may send control messages over the control links 316 and 318 to configure the RF transceivers 308 and 310, respectively, to not communicate with the implantable medical device.

An RF transceiver may selectively use different antennas in some embodiments. For example, the RF transceiver 306 may use antenna 320 or 322, the RF transceiver 308 may use antenna 324 or 326, and the RF transceiver 310 may use antenna 328 or 330. In some aspects, the ability to use different antennas at different times provides polarity and pattern diversity that may improve communication quality. For example, the processor 312 may cooperate with the RF transceivers 306, 308, and 310 to determine the communication quality associated with each antenna configuration in an attempt to identify the optimum configuration for communication with the implantable medical device.

Figure 4:
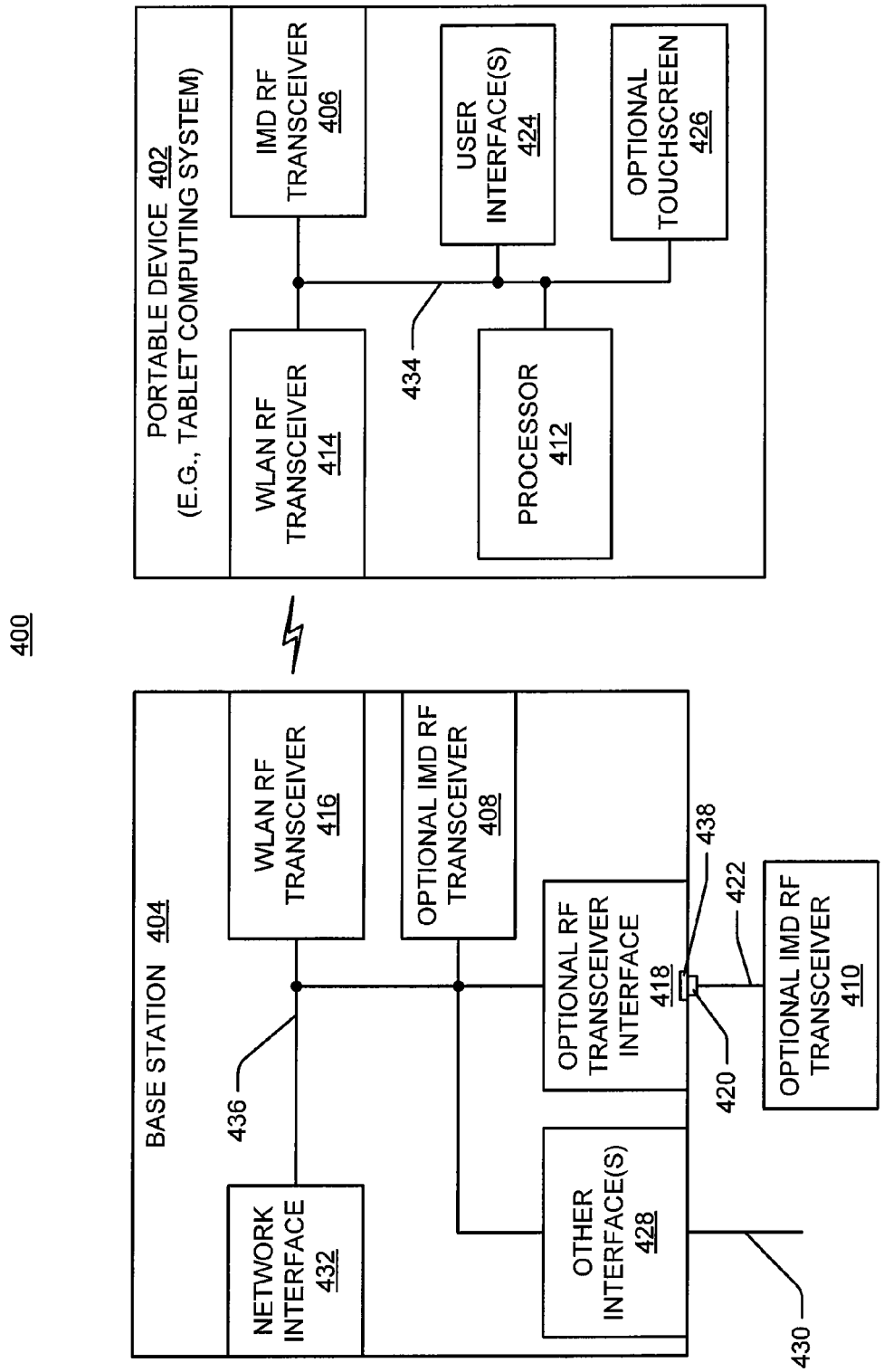
FIG. 4 is a simplified block diagram of an embodiment of a communication system where RF transceivers are deployed in different devices.

FIG. 4 illustrates an embodiment of system 400 that includes a portable device 402 (e.g., a tablet computing system) and an associated base station 404. In particular, this figure illustrates sample components that facilitate RF transceiver hopping and inter-device communication.

The portable device 402 includes an implantable medical device (IMD) RF transceiver 406, while the base station 404 employs an on-device IMD RF transceiver 408 and/or a peripheral IMD RF transceiver 410. Each of these IMD RF transceivers is configured to communicate with an implantable medical device (not shown in FIG. 4). A processor 412 located at the portable device 402 controls the selection of the RF transceivers 406, 408, and 410. In other embodiments, however, such a processor may be located at the base station 404 or at some other suitable device that is capable of communicating with the portable device 402 and the base station 404.

The portable device 402 and the base station 404 include wireless local area network (WLAN) RF transceivers 414 and 416, respectively, to enable inter-device communication. The transceivers 414 and 416 may support different types of wireless communication technologies in different embodiments. In various embodiments, the RF transceivers 414 and 416 may comprise IEEE 802.11 (i.e., Wi-Fi) transceivers, Bluetooth transceivers, Zigbee transceivers, or other types of transceivers.

The processor 412 communicates with the IMD RF transceivers 408 and 410 via the RF transceivers 414 and 416. For example, the IMD RF transceivers 408 and 410 report communication quality information to the processor 412 via one or more wireless links established through the RF transceivers 414 and 416. Conversely, the processor 412 sends control signals (e.g., to enable or disable communication with the implantable medical device) to the IMD RF transceivers 408 and 410 via the wireless link(s) established through the RF transceivers 414 and 416.

As mentioned above, in some embodiments, the base station 404 employs a peripheral RF transceiver 410. For example, the RF transceiver 410 may be detachable from the base station 404 such that the RF transceiver 410 is capable of being deployed at the base station 404 or some distance away from the base station 404. In this way, the RF transceiver 410 may be moved as needed to provide the best possible communication quality. Thus, in scenarios where the base station 404 remains stationary, improved communication performance may be achieved by simply moving the RF transceiver 410. In various embodiments, the peripheral RF transceiver 410 may be deployed at the base station 404 as the sole RF transceiver, or in conjunction with at least one other peripheral RF transceiver (not shown), or in conjunction with at least one on-device RF transceiver (e.g., the RF transceiver 408), or in conjunction with at least one other peripheral RF transceiver and at least one on-device RF transceiver. Accordingly, the teachings herein may be used to provide RF transceivers in a variety of locations to accommodate various deployment scenarios.

In the example of FIG. 4, the base station 404 may include an RF transceiver interface 418 (e.g., comprising driver and receiver circuitry) that is coupled to the RF transceiver 416 and that also includes a connector 438 that is configured to connect to a connector 420 of the RF transceiver 410. In this way, the RF transceiver 410 is electrically coupled with the RF transceiver 416 such that communication may be established between the RF transceiver 410 and the processor 412.

The connector 420 may be deployed at the RF transceiver 410 in various ways. In the example of FIG. 4, the RF transceiver 410 is coupled to the connector 420 via an electrical cable 422. For example, the RF transceiver 410 may take the form of an external adapter that plugs into a port (e.g., the connector 438) of the base station 404. In some implementations, this external adapter is referred to as a dongle. In other embodiments, a connector similar to the connector 420 may be directly attached to (or embodied within) the RF transceiver 410. For example, the RF transceiver 410 may have a form factor similar to a USB-based Bluetooth adapter. In either case, the connector 420 is electrically coupled with the RF transceiver 410 via suitable electrical conductors to provide the desired electrical coupling to the RF transceiver 416.

The processor 412 (or some other processor, not shown) provides programmer functionality for the portable device 402 in some embodiments. For example, the processor 412 may manage user interfaces 424 and an optional touchscreen 426 to enable a user to control downloading/uploading of information to/from the implantable medical device.

The base station 404 also includes components to support other medical and connectivity functionality. For example, the base station 404 includes one or more interfaces 428 for ECG cables 430 and/or other external devices. In addition, the base station 404 includes a network interface 432 that provides connectivity to a communication network (e.g., the Internet, a local area network, a medical network, etc.).

The portable device 402 and the base station 404 also include busses that provide connectivity for the components of these respective devices. In particular, one or more busses 434 are used to couple the components of the portable device 402 as needed. Similarly, one or more busses 436 are used to couple the components of the base station 404 as needed.

Figure 5:
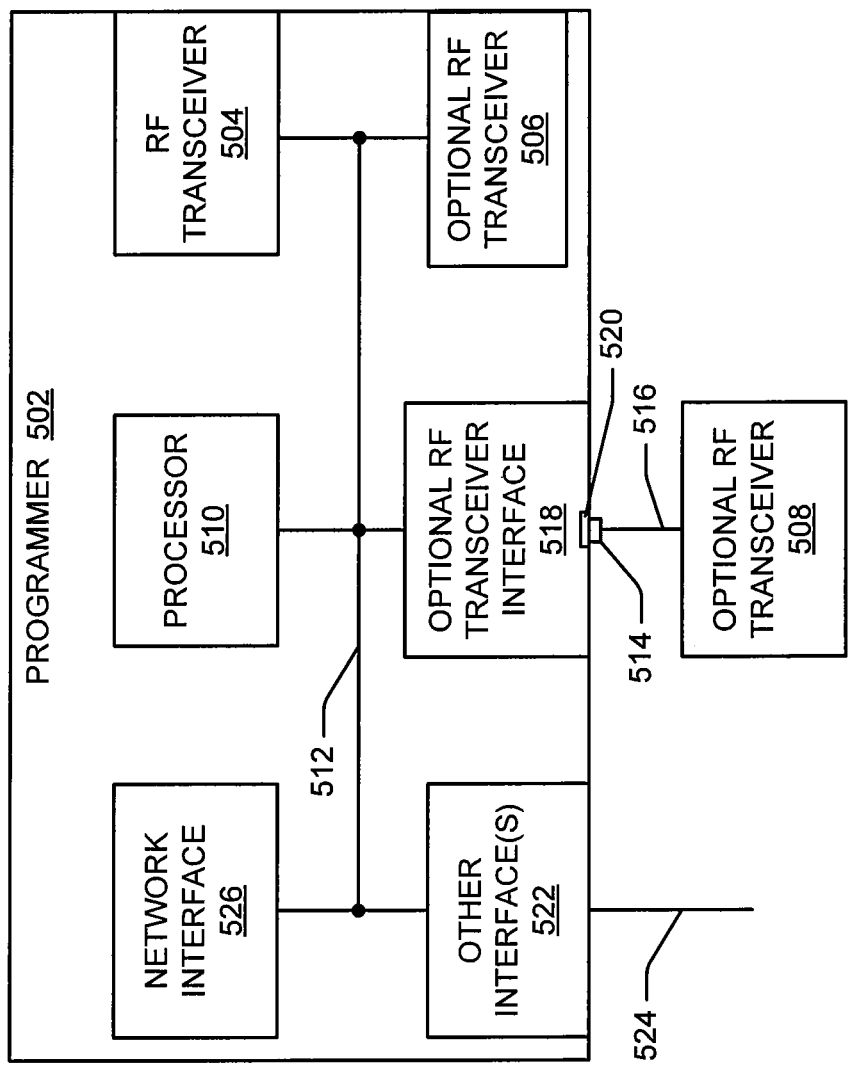
FIG. 5 is a simplified block diagram of an embodiment of a communication system where multiple RF transceivers are deployed in a single device.

FIG. 5 illustrates an embodiment where RF transceiver hopping is employed within single device. Such a device may take the form of a portable device or a more stationary device (e.g., that does not run on battery power) in different implementations. In addition, in various implementations, the device may provide functionality including, for example, implantable medical device programming functionality, home monitoring functionality, network connectivity functionality, or some combination of this or other functionality.

In the example of FIG. 5, a programmer 502 (e.g., a tablet computing system) includes an RF transceiver 504 and at least one other RF transceiver (e.g., another on-device RF transceiver 506 and/or a peripheral RF transceiver 508). A processor 510 controls the selection of the RF transceivers 504, 506, and 508 for communication with an implantable medical device (not shown). One or more busses 512 providing signaling coupling for the components of the programmer 502 as needed.

The peripheral RF transceiver 508 may be implemented in a similar manner as the peripheral RF transceiver 410 discussed above in conjunction with FIG. 4. For example, the RF transceiver 508 may be detachable from the programmer 502 to potentially provide improved communication performance by placing the RF transceiver 508 at locations remote from the programmer 502. The RF transceiver 508 includes (or interfaces with) a connector 514 that is electrically coupled to the RF transceiver 508 directly or via a cable 516 (as shown in FIG. 5).

Also, in a configuration that employs one or more peripheral RF transceivers, the programmer 502 includes an RF transceiver interface 518 that is coupled to the processor 510 and includes at least one connector 520 that is configured to connect each connector (e.g., the connector 514) of each peripheral RF transceiver. In this way, communication may be established between each peripheral RF transceiver and the processor 510.

The processor 510 (or some other processor, not shown) supports the programmer functionality of the programmer 502. For example, as discussed above at FIG. 4, the processor 510 may manage user interfaces (not shown) to enable a user to control downloading/uploading of information to/from the implantable medical device.

The programmer 502 also includes components to support other medical functionality. For example, similar to the base station 404 discussed above, the programmer 502 includes one or more interfaces 522 for ECG cables 524 and/or other external devices.

In addition, the programmer 502 includes a network interface 526 that provides connectivity to a communication network. In implementations where the programmer 502 is able to connect to a wired network, the network interface 522 may provide corresponding network connectivity (e.g., via an Ethernet transceiver). In implementations where the programmer 502 is able to connect to a wireless network (e.g., the programmer 502 is a portable device), the network interface 522 may provide wireless network connectivity (e.g., via a Wi-Fi transceiver, a cellular transceiver, etc.).

Figure 7:
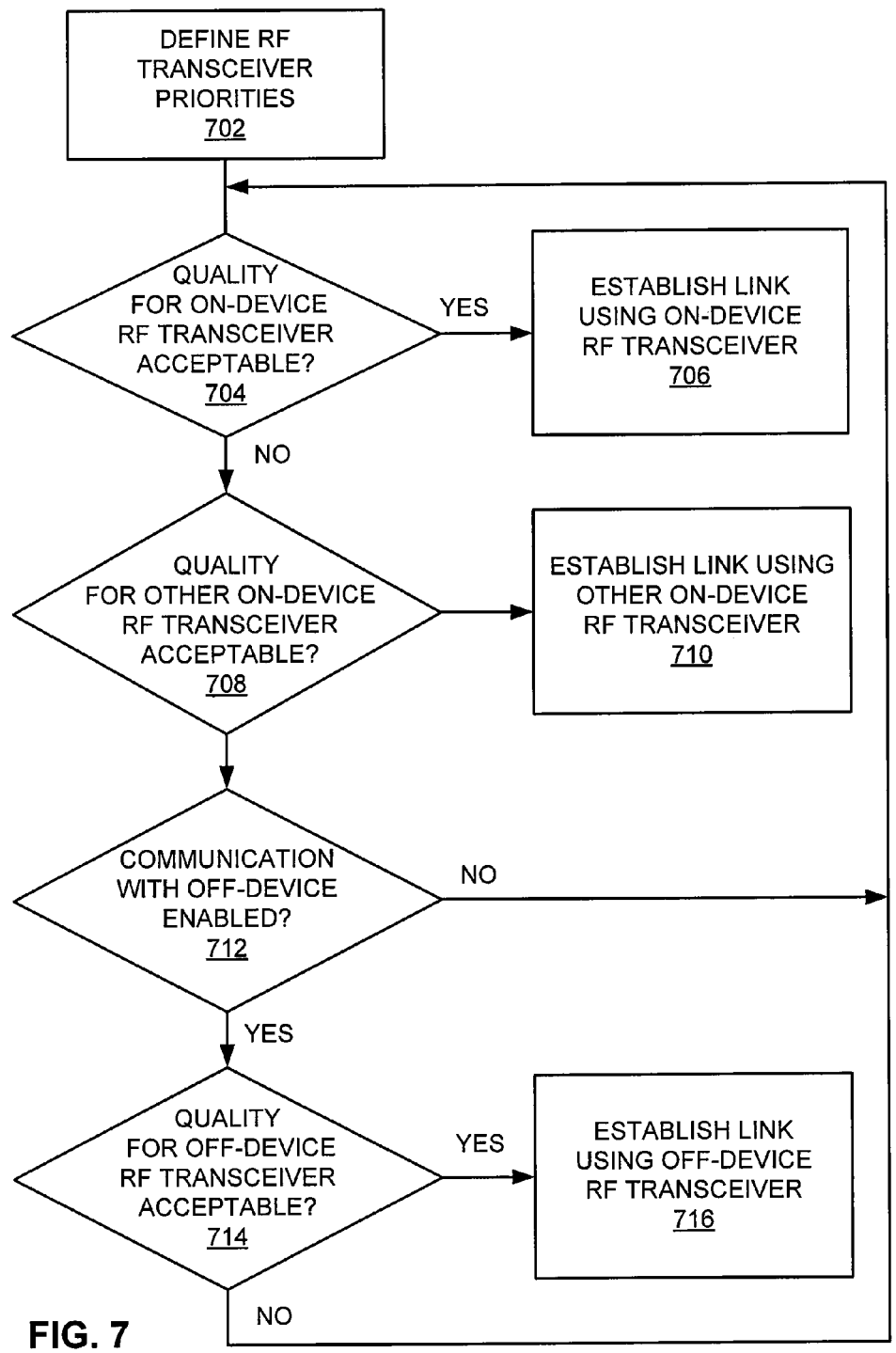
FIG. 7 is a simplified flowchart of an embodiment of operations for selecting an RF transceiver for communication with an implantable medical device based on a defined priority.
Figure 8:
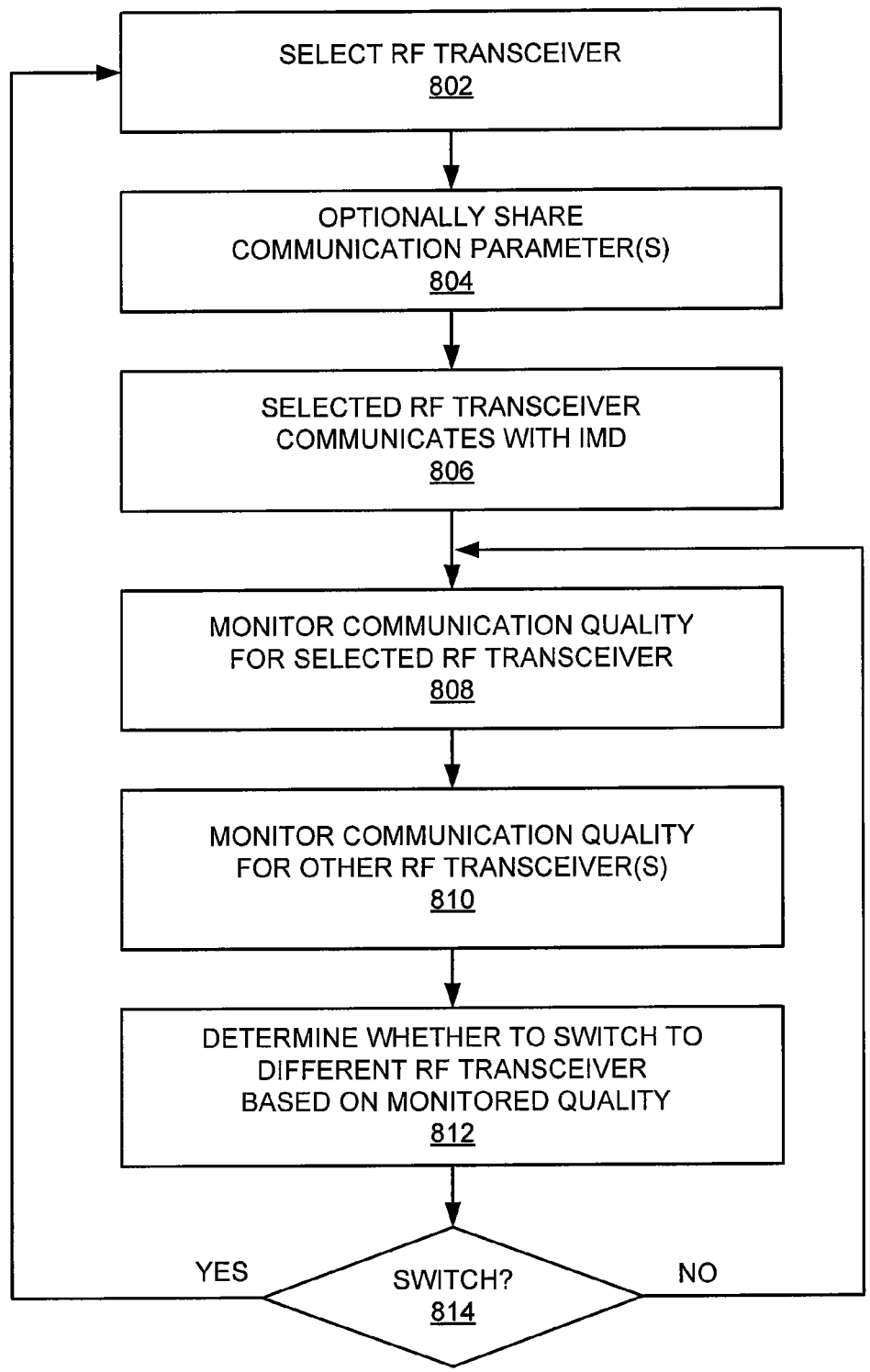
FIG. 8 is a simplified flowchart of an embodiment of operations for dynamically selecting an RF transceiver for communication with an implantable medical device based on monitoring of communication quality.

With the above in mind, several examples of operations that may be employed for an RF transceiver hopping scheme will be described with reference to the flowcharts of FIGS. 6-8. For convenience, the operations of FIGS. 6-8 (or any other operations discussed herein) may be described as being performed by specific components (e.g., any of the components of FIGS. 1-5). It should be appreciated, however, that these operations may be performed by other types of components and may be performed using a different number of components. It also should be appreciated that one or more of the operations described herein may not be employed in a given implementation.

Figure 6:
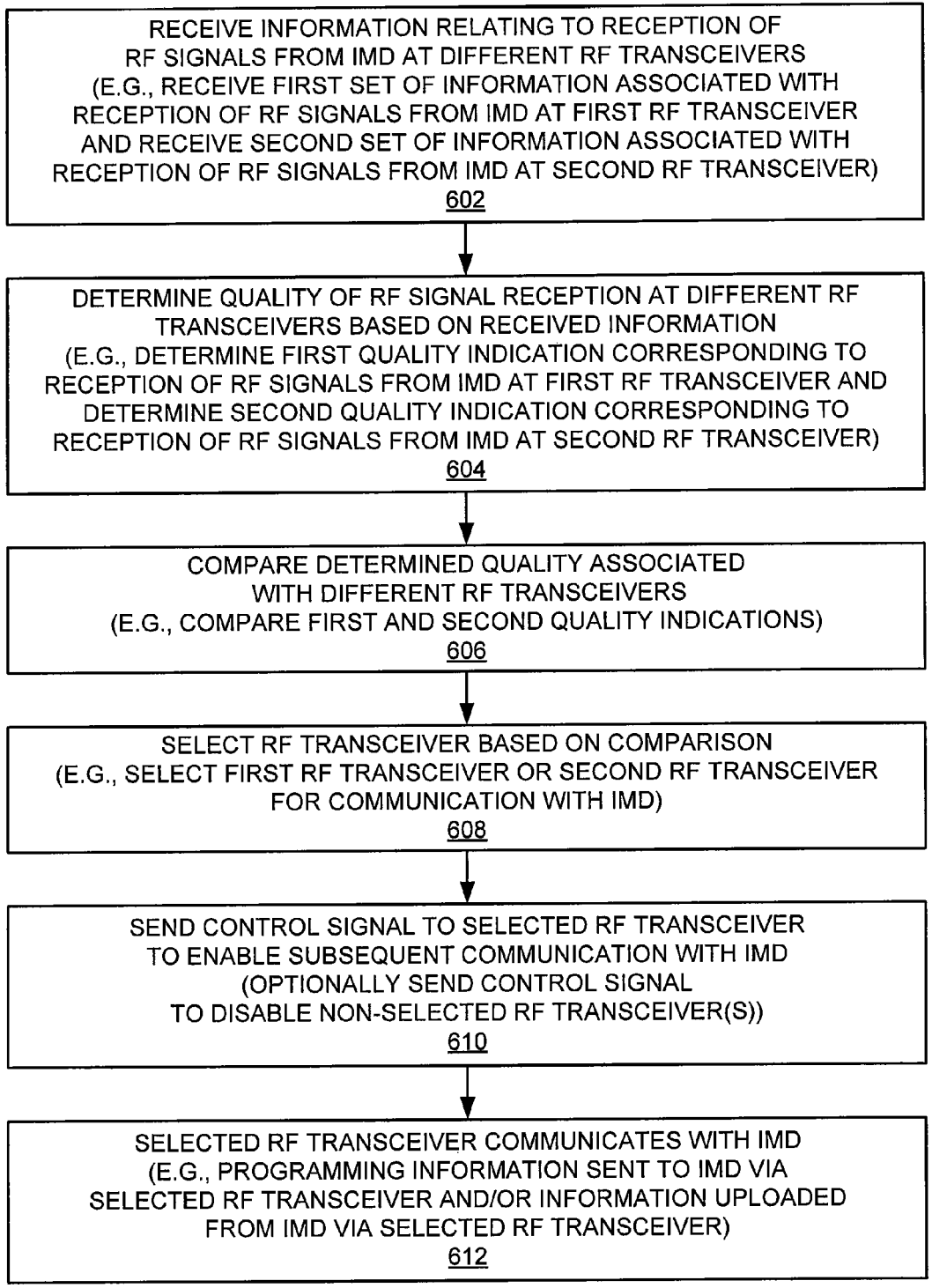
FIG. 6 is a simplified flowchart of an embodiment of operations for selecting an RF transceiver for communication with an implantable medical device.

FIG. 6 illustrates sample operations for selecting an RF transceiver that is to be used for subsequent communication with an implantable medical device. For purposes of illustration, the operations of blocks 602-610 are described as being performed by a processor.

As represented by block 602, the processor receives information relating to the reception of RF signals at different RF transceivers. For example, each of the RF transceivers may be configured to receive RF signals transmitted from a nearby implantable medical device and then send corresponding information relating to the reception of those RF signals to the processor. Thus, a first RF transceiver may send a first set of information associated with that RF transceivers received signals, a second RF transceiver may send a second set of information associated with that RF transceiver's received signals, and so on. As discussed above in conjunction with FIG. 1, in various embodiments this information may comprise information received by the RF transceivers via the RF signals (e.g., data decoded from the RF signals) or information generated by the RF transceivers (e.g., signal strength information, CRC information, etc.) as a result of receiving the RF signals.

As represented by block 604, based on the received information, the processor determines the quality of the RF signal reception at the different RF transceivers. In a sample implementation, the processor determines a first quality indication (e.g., a metric for ECC, CRC, throughput, RSSI, SNR, or TSI, etc.) corresponding to the reception of RF signals from the implantable medical device at a first RF transceiver, determines a second quality indication corresponding to the reception of RF signals from the implantable medical device at a second RF transceiver, and so on. These quality indications may be determined in various ways. In some implementations, this determination involves calculating a value based on the information received at block 602. In some implementations, this determination involves selecting the information received at block 602. As discussed above in conjunction with FIG. 1, in various embodiments these quality indications may comprises, for example, received signal strength information, CRC information, ECC information, throughput information, some other suitable information, or some combination of this information.

As represented by block 606, the processor compares the quality associated with the different RF transceivers that was determined at block 604. For example, the different quality indications associated with the different RF transceivers may be compared to identify the best quality indication. Continuing with the above example, in some cases, this involves identifying the quality indication corresponding to the highest signal strength, the highest RSSI, the highest TSI, the lowest SNR, the fewest CRC errors, the fewest ECC errors, the highest throughput, or the best value of some other metric.

As represented by block 608, based on the comparison of block 606, the processor selects one RF transceiver for RF communication with the implantable medical device. For example, the processor may identify the RF transceiver associated with the highest receive signal strength, and then elect to use that RF transceiver to download information to and upload information from the implantable medical device for the immediate future.

As represented by block 610, the processor sends a control signal to the selected RF transceiver to enable subsequent communication with the implantable medical device. In some cases, the control signal (e.g., a message) either implicitly or explicitly informs the selected RF transceiver that it is to communicate with the implantable medical device. As one example, the control signal may instruct the RF transceiver to attempt to "wake up" the implantable medical device's communication circuitry. In some cases, the control signal configures the RF transceiver with one or more communication parameters to be used for the communication with the implantable medical device. These parameters include, for example, a data rate, a communication channel, an identifier of the implantable medical device, an identifier associated with an external device (e.g., a programmer), wake-up parameters, and so on.

In some implementations, the processor also sends control signals to the RF transceivers that were not selected at block 608 (the non-selected RF transceivers) to set each of the non-selected RF transceivers to a low power mode. In this way, the battery life of a portable device may be extended and/or potential interference from these RF transceivers mitigated.

In other implementations, each RF transceiver defaults to a low power mode and only switches to a higher power mode (e.g., actively receiving and transmitting) upon receiving a control signal that indicates that the RF transceiver is to, for example, commence communication with the implantable medical device. In these implementations, "switch to low power mode" control signals may not be sent to the non-selected RF transceivers.

As represented by block 612, the selected RF transceiver communicates with the implantable medical device as needed. Accordingly, when a user of a programmer operates a user interface to invoke programming operations, the corresponding programming information is sent to the selected RF transceiver (e.g., by the processor), whereupon this RF transceiver transmits the information to the implantable medical device via, for example, an MICS band or an ISM band. Conversely, when a user of a programmer operates a user interface to invoke upload operations, the selected RF transceiver cooperates with the implantable medical device to receive the specified information from the implantable medical device.

As discussed in more detail below, the above operations are typically repeated to determine additional quality indications over time. These quality indications are then compared to determine whether another RF transceiver is associated with a higher quality indication than the previously selected RF transceiver. If so, the other RF transceiver is selected for subsequent communication with the implantable medical device instead of the previously selected RF transceiver.

In some embodiments, the RF transceivers are prioritized such that an external communication device (e.g., a portable programmer) will give priority to certain RF transceivers when determining which RF transceiver is to be used for communicating with an implantable medical device. FIG. 7 illustrates sample operations where on-device RF transceivers have highest priority and off-device RF transceivers have lower priority. Here, it is assumed that two on-device RF transceivers are available and an off-device RF transceiver may be available. It should be appreciated, however, that a different number of on-device and/or off-device RF transceivers may be used in different implementations.

As represented by block 702, the priority of the RF transceivers is defined. For example, prior to commencing RF communication with an implantable medical device (e.g., upon deployment of a portable programmer), a first on-device RF transceiver may be assigned a highest priority, a second on-device RF transceiver may be assigned a lower priority, and an off-device RF transceiver may be assigned a lowest priority.

As represented by block 704, once it is desired to commence RF communication with the implantable medical device, the quality for the highest priority RF transceiver is checked to see if it is acceptable. For example, a quality indication (e.g., received signal strength) may be compared to a threshold value that has been deemed to be indicative of a good communication link with the implantable medical device.

As represented by block 706, if the quality checked at block 704 is acceptable, a communication link with the implantable medical device is established using the highest priority on-device RF transceiver. That is, in this example, the quality of other RF transceivers may not be checked if the highest priority RF transceiver provides an acceptable communication link with the implantable medical device.

If the quality checked at block 704 is not acceptable, the search for an acceptable RF transceiver continues. In the example of FIG. 7, the second on-device RF transceiver has the next highest priority.

As represented by block 708, the quality for the second on-device RF transceiver is checked to see if it is acceptable. As represented by block 710, if the quality checked at block 708 is acceptable, a communication link with the implantable medical device is established using this on-device RF transceiver.

If the quality checked at block 708 is not acceptable, the search for an acceptable RF transceiver continues. In the example of FIG. 7, the off-device RF transceiver has the next highest priority. As represented by block 712, a determination is made as to whether communication with this off-device RF transceiver is enabled. If not, the operational flow proceeds back to block 704 to continue the search accordingly to the defined priority. That is, the quality of the RF transceiver circuits is repeatedly monitored in anticipation of an improvement in the RF conditions. In some cases, an error message may be sent to the operator of the communication device in the event an appropriate RF transceiver is not identified within a defined period of time.

As represented by block 714, if communication with the off-device RF transceiver is enabled, the quality for the off-device RF transceiver is checked to see if it is acceptable. As represented by block 716, if the quality checked at block 714 is acceptable, a communication link with the implantable medical device is established using this off-device RF transceiver. If the quality checked at block 714 is not acceptable, the operational flow proceeds back to block 704 to continue the search accordingly to the defined priority.

As mentioned above, an RF transceiver hopping scheme may dynamically select the RF transceiver that is able to establish the highest quality communication with an implantable medical device at a given point in time. FIG. 8 illustrates sample operations where the communication quality associated with different RF transceivers is monitored over time in an attempt to ensure that the RF transceiver that currently provides the best performance is selected. In this case, rather than simply selecting the first identified RF transceiver with acceptable quality, the quality of each RF transceivers is checked to identify the best RF transceiver.

As represented by block 802, at some point in time, an RF transceiver is selected for communication with an implantable medical device. This initial selection may be made, for example, based on a default RF transceiver, based on the later described operations of FIG. 8, or based on some other selection criterion. As discussed above, several operational parameters may be specified in conjunction with selecting an RF transceiver. For example, the antenna and/or at least one communication parameter to be used by the selected RF transceiver may be specified.

As represented by block 804, in some implementations, the communication parameter(s) specified for the selected RF transceiver are shared with the non-selected RF transceivers. For example, a processor that controls the selection may determine the parameter(s) and then send the parameter(s) to each of the non-selected RF transceivers. Each non-selected RF transceiver may then use the received parameter(s) to monitor the RF communication between the selected RF transceiver and the implantable medical device.

In this way, a given non-selected RF transceiver may be configured to readily take over the RF communication in the event that RF transceiver is subsequently selected to provide the RF communication with the implantable medical device. Thus, in some aspects, the non-selected RF transceivers are configured as clones of the selected RF transceiver (e.g., by maintaining the same state as the selected RF transceiver).

In addition, each non-selected RF transceiver may be configured to process (e.g., decode) the information being sent between the selected RF transceiver and the implantable medical device. In this way, it may be determined, for example, whether a given non-selected RF transceiver would be able to provide a better communication link with the implantable medical device (e.g., as evidenced by a lower CRC error rate for decoded data).

As represented by block 806, at some point in time, the RF transceiver selected at block 802 communicates with the implantable medical device. For example, the RF transceiver may wake the implantable medical device's communication circuitry and then upload/download information as required.

As represented by block 808, the quality of the communication for the selected RF transceiver is monitored over time (e.g., at defined intervals). For example, a record may be made of the received signal strength seen at the RF transceiver over time. As another example, a record may be made of the CRC and/or ECC errors (e.g., number of errors, error rate, etc.) detected in the data sent between the RF transceiver and the implantable medical device over time. As yet another example, a record may be made of the throughput for the data flow between the RF transceiver and the implantable medical device over time.

As discussed above, the monitoring of communication quality may involve determining the quality associated with the use of different antennas. Thus, the selected RF transceiver may be configured (e.g., instructed) to receive RF signals using different antennas so that a quality indication may be determined for each antenna configuration. For example, a processor that controls the selection may identify the antenna to be used for RF communication and configure the RF transceiver to use the identified antenna. The processor may then determine the quality indication corresponding to that antenna configuration based on signals received by the selected RF transceiver via the identified antenna.

As represented by block 810, communication quality for each of the non-selected RF transceivers is also monitored over time. For example, the receivers of these RF transceivers may be enabled such that one or more of the above quality indications (e.g., received signal strength, received CRC errors, received ECC errors, received throughput) can be determined. As mentioned above, this monitoring may be accomplished by cloning of the selected RF transceiver at the non-selected RF transceivers. In addition, this monitoring may involve the use of different antennas for a given RF transceiver. Thus, the processor may identify the antennas to be used by the non-selected transceivers, configure the use of these antennas, and determine the quality indications associated with these antenna configurations.

As represented by blocks 812 and 814, a determination as to whether to switch to a different RF transceiver is made based on the quality monitoring of blocks 808 and 810. For example, upon determining that a non-selected RF transceiver has better quality that the selected RF transceiver, a decision may be made to select the better RF transceiver. In some cases, this determination is based on whether certain thresholds are met (e.g., a quality indication of a second RF transceiver has exceeded the quality indication of a first RF transceiver by at least specified amount for at least a specified period of time).

In the event a decision to switch is made at block 814, the operational flow proceeds to block 802 where the new RF transceiver is selected for communication with the implantable medical device. In the event a decision to not switch is made at block 814, the operational flow proceeds to block 808 and monitoring of the selected and non-selected RF transceivers continues.

The selection of an RF transceiver may be accomplished in a variety of ways consistent with the teachings herein. In some cases a combination of a prioritized scheme and a comparison scheme is employed. For example, if the RF transceiver currently being checked has a quality that is less than or equal to a first threshold, this RF transceiver is temporarily eliminated from the search and the search continues to the next lowest priority RF transceiver. If the RF transceiver currently being checked has a quality greater than or equal to a second threshold (higher than the first threshold), that RF transceiver is selected for communication with the implantable medical device. If the RF transceiver currently being checked has a quality that is between the first threshold and the second threshold, the search continues to the next lowest priority RF transceiver to see if it has a higher quality. This process is then repeated, as necessary for the other RF transceivers accordingly to the defined priority. It should be appreciated that other selection schemes may be employed in other cases.

Figure 9:
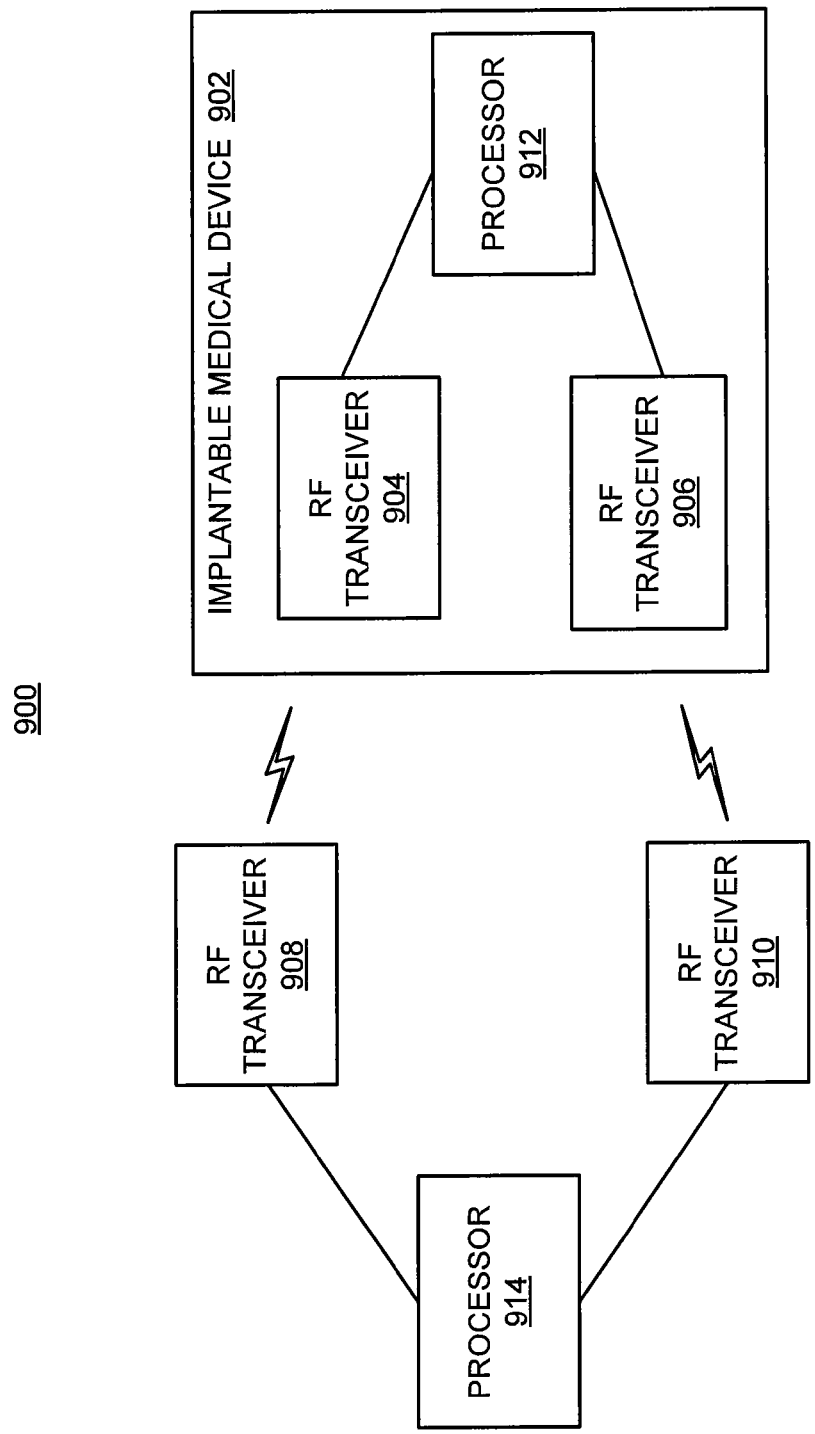
FIG. 9 is a simplified diagram of an embodiment of a communication system where at least one external RF transceiver circuit is selected to communicate with at least one RF transceiver circuit of an implantable medical device.

In some embodiments, an implantable medical device includes multiple RF transceivers to facilitate higher quality communication with external devices. FIG. 9 illustrates a sample embodiment of a system 900 where an implantable medical device 902 includes an RF transceiver 904 and an RF transceiver 906, either or both of which may communicate with external RF transceivers 908 and 910. A processor 912 of the implantable medical device 902 controls the operation of (e.g., the selection of) the RF transceivers 904 and 906, while a processor 914 controls the operation of the RF transceivers 908 and 910.

In some cases, the implantable medical device 902 uses one of the RF transceivers 904 and 906 to communicate with one of the external RF transceivers 908 and 910. For example, upon determining that the communication quality associated with one of the RF transceivers 904 and 906 is unacceptable (e.g., using techniques similar to those taught herein), the processor 912 selects the other RF transceiver for communication with one of the RF transceivers 908 and 910. The processor 914 may perform complementary operations to select the external RF transceiver 908 or 910 that is to be used for communication with the selected internal RF transceiver 904 or 906. In cases where one or more of the RF transceivers is associated with multiple antennas, antenna selection techniques (e.g., as taught herein) also may be employed in conjunction with selecting the RF transceivers.

In some cases, the implantable medical device 902 uses both of the RF transceivers 904 and 906 to communicate with both of the external RF transceivers 908 and 910. In this case, a higher overall throughput may be achieved by using parallel communication links. For example, upon determining that the communication quality associated with both of the RF transceivers 904 and 906 is acceptable (e.g., using techniques similar to those taught herein), the processor 912 selects both RF transceivers for communication with both of the RF transceivers 908 and 910. The processor 912 and/or the processor 914 may then select (e.g. based on quality determinations) the specific external RF transceiver 908 or 910 that is to be used for communication with a given internal RF transceiver 904 or 906. Also, in cases where one or more of the RF transceivers is associated with multiple antennas, antenna selection techniques (e.g., as taught herein) may be employed in conjunction with selecting the RF transceivers.

Exemplary Cardiac Device

The following description sets forth an exemplary implantable cardiac device (e.g., a stimulation device such as an implantable cardioverter defibrillator, a pacemaker, etc.) that is capable of being used in connection with the various embodiments that are described herein. It is to be appreciated and understood that other medical devices, including those that are not necessarily implantable, can be used and that the description below is given, in its specific context, to assist the reader in understanding, with more clarity, the embodiments described herein.

Figure 10:
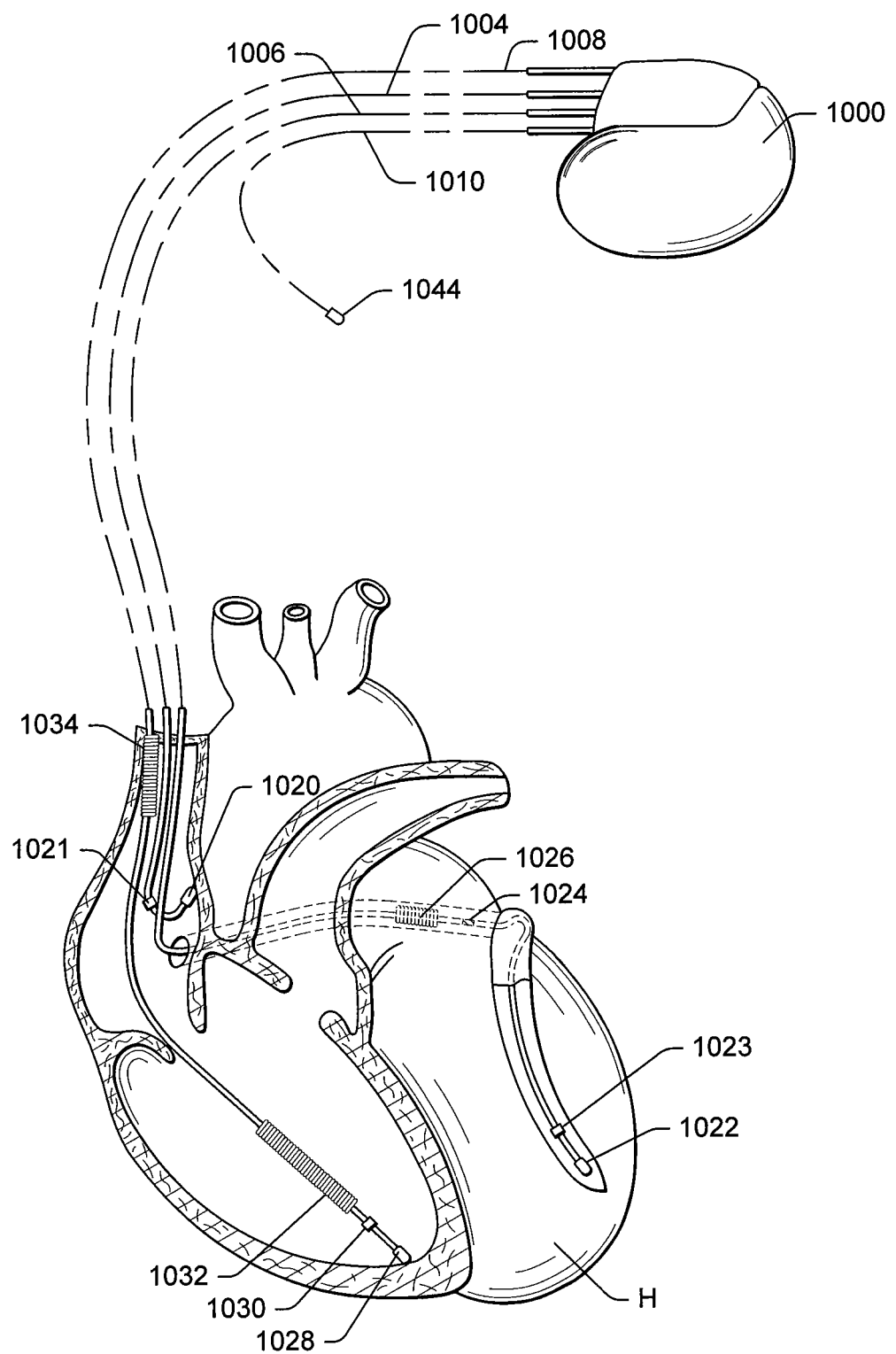
FIG. 10 is a simplified diagram of an embodiment of an implantable medical device in electrical communication with one or more leads implanted in a patient's heart for sensing conditions in the patient, delivering therapy to the patient, or providing some combination thereof.

FIG. 10 shows an exemplary implantable cardiac device 1000 in electrical communication with a patient's heart H by way of three leads 1004, 1006, and 1008, suitable for delivering multi-chamber stimulation and shock therapy. Bodies of the leads 1004, 1006, and 1008 may be formed of silicone, polyurethane, plastic, or similar biocompatible materials to facilitate implant within a patient. Each lead includes one or more conductors, each of which may couple one or more electrodes incorporated into the lead to a connector on the proximal end of the lead. Each connector, in turn, is configured to couple with a complimentary connector (e.g., implemented within a header) of the device 1000.

To sense atrial cardiac signals and to provide right atrial chamber stimulation therapy, the device 1000 is coupled to an implantable right atrial lead 1004 having, for example, an atrial tip electrode 1020, which typically is implanted in the patient's right atrial appendage or septum. FIG. 10 also shows the right atrial lead 1004 as having an optional atrial ring electrode 1021.

To sense left atrial and ventricular cardiac signals and to provide left chamber pacing therapy, the device 1000 is coupled to a coronary sinus lead 1006 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 1006 is designed to receive atrial and ventricular cardiac signals and to deliver left ventricular pacing therapy using, for example, a left ventricular tip electrode 1022 and, optionally, a left ventricular ring electrode 1023; provide left atrial pacing therapy using, for example, a left atrial ring electrode 1024; and provide shocking therapy using, for example, a left atrial coil electrode 1026 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 1000 is also shown in electrical communication with the patient's heart H by way of an implantable right ventricular lead 1008 having, in this implementation, a right ventricular tip electrode 1028, a right ventricular ring electrode 1030, a right ventricular (RV) coil electrode 1032 (or other electrode capable of delivering a shock), and a superior vena cava (SVC) coil electrode 1034 (or other electrode capable of delivering a shock). Typically, the right ventricular lead 1008 is transvenously inserted into the heart H to place the right ventricular tip electrode 1028 in the right ventricular apex so that the RV coil electrode 1032 will be positioned in the right ventricle and the SVC coil electrode 1034 will be positioned in the superior vena cava. Accordingly, the right ventricular lead 1008 is capable of sensing or receiving cardiac signals, and delivering stimulation in the form of pacing and shock therapy to the right ventricle.

The device 1000 is also shown in electrical communication with a lead 1010 including one or more components 1044 such as a physiologic sensor. The component 1044 may be positioned in, near or remote from the heart.

It should be appreciated that the device 1000 may connect to leads other than those specifically shown. In addition, the leads connected to the device 1000 may include components other than those specifically shown. For example, a lead may include other types of electrodes, sensors or devices that serve to otherwise interact with a patient or the surroundings.

Figure 11:
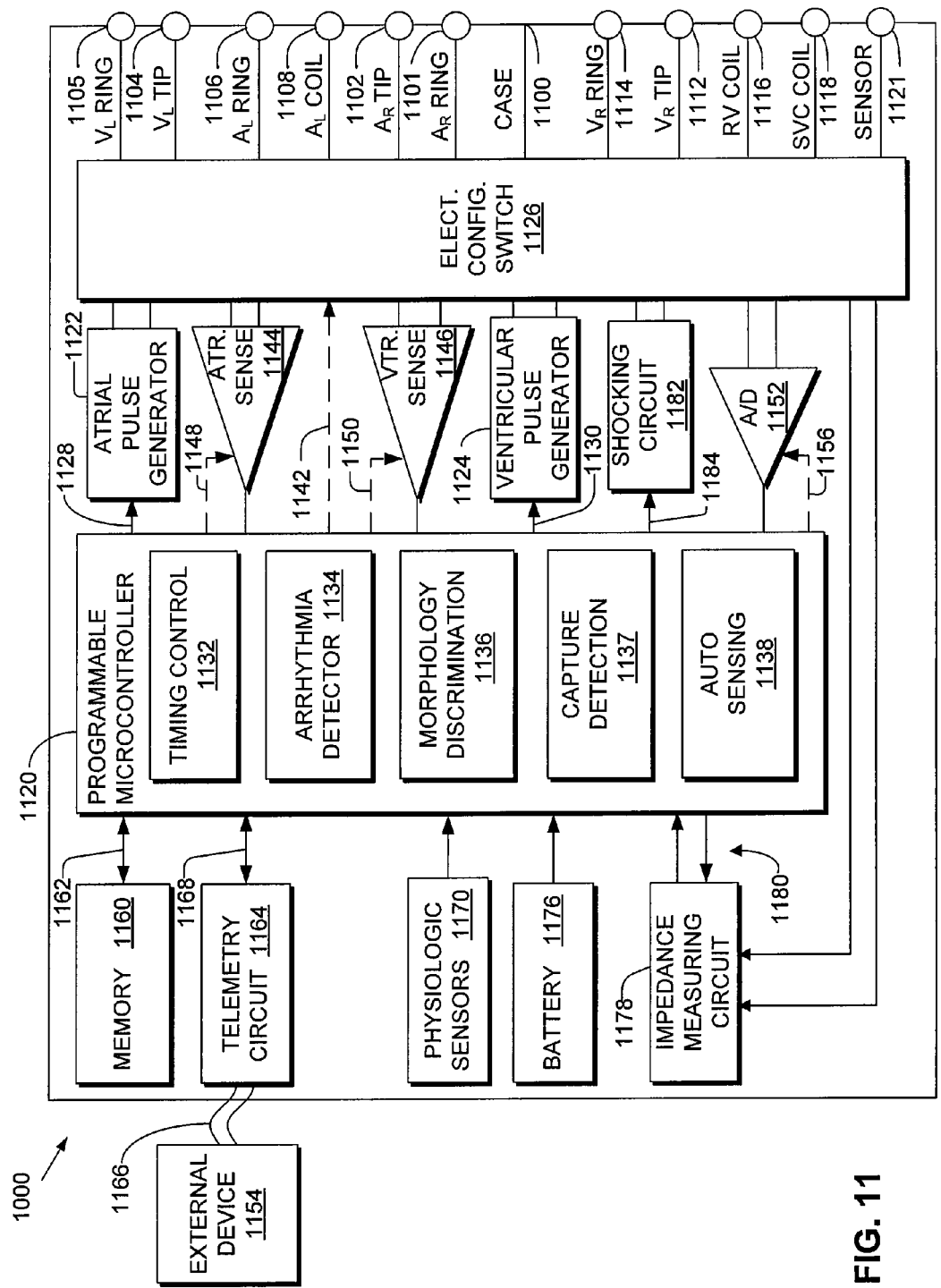
FIG. 11 is a simplified functional block diagram of an embodiment of an implantable medical device, illustrating basic elements that may be configured to sense conditions in a patient, deliver therapy to the patient, or provide some combination thereof.

FIG. 11 depicts an exemplary, simplified block diagram illustrating sample components of the device 1000. The device 1000 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

A housing 1100 for the device 1000 is often referred to as the "can", "case" or "case electrode", and may be programmably selected to act as the return electrode for all "unipolar"

modes. The housing 1100 may further be used as a return electrode alone or in combination with one or more of the coil electrodes 1026, 1032 and 1034 for shocking purposes. The housing 1100 may be constructed of a biocompatible material (e.g., titanium) to facilitate implant within a patient.

The housing 1100 further includes a connector (not shown) having a plurality of terminals 1101, 1102, 1104, 1105, 1106, 1108, 1112, 1114, 1116 and 1118 (shown schematically and, for convenience, the names of the electrodes to which they are connected are shown next to the terminals). The connector may be configured to include various other terminals (e.g., terminal 1121 coupled to a sensor or some other component) depending on the requirements of a given application.

To achieve right atrial sensing and pacing, the connector includes, for example, a right atrial tip terminal (AR TIP) 1102 adapted for connection to the right atrial tip electrode 1020. A right atrial ring terminal (AR RING) 1101 may also be included and adapted for connection to the right atrial ring electrode 1021. To achieve left chamber sensing, pacing, and shocking, the connector includes, for example, a left ventricular tip terminal (VL TIP) 1104, a left ventricular ring terminal (VL RING) 1105, a left atrial ring terminal (AL RING) 1106, and a left atrial shocking terminal (AL COIL) 1108, which are adapted for connection to the left ventricular tip electrode 1022, the left ventricular ring electrode 1023, the left atrial ring electrode 1024, and the left atrial coil electrode 1026, respectively.

To support right chamber sensing, pacing, and shocking, the connector further includes a right ventricular tip terminal (VR TIP) 1112, a right ventricular ring terminal (VR RING) 1114, a right ventricular shocking terminal (RV COIL) 1116, and a superior vena cava shocking terminal (SVC COIL) 1118, which are adapted for connection to the right ventricular tip electrode 1028, the right ventricular ring electrode 1030, the RV coil electrode 1032, and the SVC coil electrode 1034, respectively.

At the core of the device 1000 is a programmable microcontroller 1120 that controls the various modes of stimulation therapy. As is well known in the art, microcontroller 1120 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 1120 includes the ability to process or monitor input signals (data or information) as controlled by a program code stored in a designated block of memory. The type of microcontroller is not critical to the described implementations. Rather, any suitable microcontroller 1120 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 11 also shows an atrial pulse generator 1122 and a ventricular pulse generator 1124 that generate pacing stimulation pulses for delivery by the right atrial lead 1004, the coronary sinus lead 1006, the right ventricular lead 1008, or some combination of these leads via an electrode configuration switch 1126. It is understood that in order to provide stimulation therapy in each of the four chambers of the heart, the atrial and ventricular pulse generators 1122 and 1124 may include dedicated, independent pulse generators, multiplexed pulse generators, or shared pulse generators. The pulse generators 1122 and 1124 are controlled by the microcontroller 1120 via appropriate control signals 1128 and 1130, respectively, to trigger or inhibit the stimulation pulses.

Microcontroller 1120 further includes timing control circuitry 1132 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 1120 further includes an arrhythmia detector 1134. The arrhythmia detector 1134 may be utilized by the device 1000 for determining desirable times to administer various therapies. The arrhythmia detector 1134 may be implemented, for example, in hardware as part of the microcontroller 1120, or as software/firmware instructions programmed into the device 1000 and executed on the microcontroller 1120 during certain modes of operation.

Microcontroller 1120 may include a morphology discrimination module 1136, a capture detection module 1137 and an auto sensing module 1138. These modules are optionally used to implement various exemplary recognition algorithms or methods. The aforementioned components may be implemented, for example, in hardware as part of the microcontroller 1120, or as software/firmware instructions programmed into the device 1000 and executed on the microcontroller 1120 during certain modes of operation.

The electrode configuration switch 1126 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 1126, in response to a control signal 1142 from the microcontroller 1120, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 1144 and ventricular sensing circuits (VTR. SENSE) 1146 may also be selectively coupled to the right atrial lead 1004, coronary sinus lead 1006, and the right ventricular lead 1008, through the switch 1126 for detecting the presence of cardiac activity in each of the four chambers of the heart. Accordingly, the atrial and ventricular sensing circuits 1144 and 1146 may include dedicated sense amplifiers, multiplexed amplifiers, or shared amplifiers. Switch 1126 determines the "sensing polarity" of the cardiac signal by selectively closing the appropriate switches, as is also known in the art. In this way, the clinician may program the sensing polarity independent of the stimulation polarity. The sensing circuits (e.g., circuits 1144 and 1146) are optionally capable of obtaining information indicative of tissue capture.

Each sensing circuit 1144 and 1146 preferably employs one or more low power, precision amplifiers with programmable gain, automatic gain control, bandpass filtering, a threshold detection circuit, or some combination of these components, to selectively sense the cardiac signal of interest. The automatic gain control enables the device 1000 to deal effectively with the difficult problem of sensing the low amplitude signal characteristics of atrial or ventricular fibrillation.

The outputs of the atrial and ventricular sensing circuits 1144 and 1146 are connected to the microcontroller 1120, which, in turn, is able to trigger or inhibit the atrial and ventricular pulse generators 1122 and 1124, respectively, in a demand fashion in response to the absence or presence of cardiac activity in the appropriate chambers of the heart. Furthermore, as described herein, the microcontroller 1120 is also capable of analyzing information output from the sensing circuits 1144 and 1146, a data acquisition system 1152, or both. This information may be used to determine or detect whether and to what degree tissue capture has occurred and to program a pulse, or pulses, in response to such determinations. The sensing circuits 1144 and 1146, in turn, receive control signals over signal lines 1148 and 1150, respectively, from the microcontroller 1120 for purposes of controlling the gain, threshold, polarization charge removal circuitry (not shown), and the timing of any blocking circuitry (not shown) coupled to the inputs of the sensing circuits 1144 and 1146 as is known in the art.

For arrhythmia detection, the device 1000 utilizes the atrial and ventricular sensing circuits 1144 and 1146 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 1134 of the microcontroller 1120 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 1152. The data acquisition system 1152 is configured (e.g., via signal line 1156) to acquire intracardiac electrogram ("IEGM") signals or other signals, convert the raw analog data into a digital signal, and store the digital signals for later processing, for telemetric transmission to an external device 1154, or both. For example, the data acquisition system 1152 may be coupled to the right atrial lead 1004, the coronary sinus lead 1006, the right ventricular lead 1008 and other leads through the switch 1126 to sample cardiac signals across any pair of desired electrodes.

The data acquisition system 1152 also may be coupled to receive signals from other input devices. For example, the data acquisition system 1152 may sample signals from a physiologic sensor 1170 or other components shown in FIG. 11 (connections not shown).

The microcontroller 1120 is further coupled to a memory 1160 by a suitable data/address bus 1162, wherein the programmable operating parameters used by the microcontroller 1120 are stored and modified, as required, in order to customize the operation of the device 1000 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 1152), which data may then be used for subsequent analysis to guide the programming of the device 1000.

Advantageously, the operating parameters of the implantable device 1000 may be non-invasively programmed into the memory 1160 through a telemetry circuit 1164 in telemetric communication via communication link 1166 with the external device 1154, such as a programmer, transtelephonic transceiver, a diagnostic system analyzer or some other device. The microcontroller 1120 activates the telemetry circuit 1164 with a control signal (e.g., via bus 1168). The telemetry circuit 1164 advantageously allows intracardiac electrograms and status information relating to the operation of the device 1000 (as contained in the microcontroller 1120 or memory 1160) to be sent to the external device 1154 through an established communication link 1166: The telemetry circuit 1164 and the external device 1154 may each employ one or more RF transceivers and associated RF transceiver selection functionality as taught herein.

The device 1000 can further include one or more physiologic sensors 1170. In some embodiments the device 1000 may include a "rate-responsive" sensor that may provide, for example, information to aid in adjustment of pacing stimulation rate according to the exercise state of the patient. One or more physiologic sensors 1170 (e.g., a pressure sensor) may further be used to detect changes in cardiac output, changes in the physiological condition of the heart, or diurnal changes in activity (e.g., detecting sleep and wake states). Accordingly, the microcontroller 1120 responds by adjusting the various pacing parameters (such as rate, A-V Delay, V-V Delay, etc.) at which the atrial and ventricular pulse generators 1122 and 1124 generate stimulation pulses.

While shown as being included within the device 1000, it is to be understood that a physiologic sensor 1170 may also be external to the device 1000, yet still be implanted within or carried by the patient. Examples of physiologic sensors that may be implemented in conjunction with the device 1000 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 1170 may optionally include one or more of components to help detect movement (via, e.g., a position sensor or an accelerometer) and minute ventilation (via an MV sensor) in the patient. Signals generated by the position sensor and MV sensor may be passed to the microcontroller 1120 for analysis in determining whether to adjust the pacing rate, etc. The microcontroller 1120 may thus monitor the signals for indications of the patient's position and activity status, such as whether the patient is climbing up stairs or descending down stairs or whether the patient is sitting up after lying down.

The device 1000 additionally includes a battery 1176 that provides operating power to all of the circuits shown in FIG. 11. For a device 1000 which employs shocking therapy, the battery 1176 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 1176 also desirably has a predictable discharge characteristic so that elective replacement time can be detected. Accordingly, the device 1000 preferably employs lithium or other suitable battery technology.

The device 1000 can further include magnet detection circuitry (not shown), coupled to the microcontroller 1120, to detect when a magnet is placed over the device 1000. A magnet may be used by a clinician to perform various test functions of the device 1000 and to signal the microcontroller 1120 that the external device 1154 is in place to receive data from or transmit data to the microcontroller 1120 through the telemetry circuit 1164.

The device 1000 further includes an impedance measuring circuit 1178 that is enabled by the microcontroller 1120 via a control signal 1180. The known uses for an impedance measuring circuit 1178 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 1000 has been implanted; measuring stroke volume; and detecting the opening of heart valves, etc. The impedance measuring circuit 1178 is advantageously coupled to the switch 1126 so that any desired electrode may be used.

In the case where the device 1000 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 1120 further controls a shocking circuit 1182 by way of a control signal 1184. The shocking circuit 1182 generates shocking pulses of low (e.g., up to 0.5 J), moderate (e.g., 0.5 J to 10 J), or high energy (e.g., 11 J to 40 J), as controlled by the microcontroller 1120. Such shocking pulses are applied to the patient's heart H through, for example, two shocking electrodes and as shown in this embodiment, selected from the left atrial coil electrode 1026, the RV coil electrode 1032 and the SVC coil electrode 1034. As noted above, the housing 1100 may act as an active electrode in combination with the RV coil electrode 1032, as part of a split electrical vector using the SVC coil electrode 1034 or the left atrial coil electrode 1026 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining to the treatment of fibrillation. Accordingly, the microcontroller 1120 is capable of controlling the synchronous or asynchronous delivery of the shocking pulses.

As mentioned above, the device 1000 may include several components that provide RF transceiver selection-related functionality as taught herein. For example, the microcontroller 1120 (e.g., a processor providing signal processing functionality) may implement or support at least a portion of the RF transceiver selection functionality discussed herein for an implementation that employs multiple RF transceivers.

Various modifications may be incorporated into the disclosed embodiments based on the teachings herein. For example, the structure and functionality taught herein may be incorporated into types of devices other than the specific types of devices described above. Different embodiments of such an apparatus may include a variety of hardware and software processing components. In some embodiments, hardware components such as processors, controllers, state machines, logic, or some combination of these components, may be used to implement one or more of the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways. For example, electrical conductor-based electrical coupling (e.g., in the form of traces on a printed circuit board, wires, etc.) are typically employed between on-device components.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of A, B, or C" or "one or more of A, B, or C" or "at least one of the group consisting of A, B, and C" used in the description or the claims means "A or B or C or any combination of these elements."

As used herein, the term "determining" encompasses a wide variety of actions. For example, "determining" may include calculating, computing, processing, deriving, investigating, looking up (e.g., looking up in a table, a database or another data structure), ascertaining, and the like. Also, "determining" may include receiving (e.g., receiving information), accessing (e.g., accessing data in a memory), and the like. Also, "determining" may include resolving, selecting, choosing, establishing, and the like.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above it will be understood that the teachings herein are intended to cover any changes, adaptations or modifications which are within the scope of the disclosure.

What is claimed is:

1. A communication device for communicating with an implantable medical device, comprising:
    a first radiofrequency transceiver circuit configured to receive radiofrequency signals from an implantable medical device;
    at least one other radiofrequency transceiver circuit configured to receive radiofrequency signals from an implantable medical device; and
    a processing circuit configured to:
    determine a first quality indication corresponding to reception of the radiofrequency signals from the implantable medical device by the first radiofrequency transceiver circuit;
    determine at least one other quality indication corresponding to reception of radiofrequency signals from the implantable medical device by the at least one other radiofrequency transceiver circuit;
    compare the first quality indication and the at least one other quality indication; and
    select a first one of the radiofrequency transceiver circuits for radiofrequency communication with the implantable medical device, wherein the selection is based on the comparison.

2. The communication device of claim 1, wherein the processing circuit is further configured to:
    determine additional quality indications that correspond to reception of other radiofrequency signals from the implantable medical device by the radiofrequency transceiver circuits;
    compare the additional quality indications;
    determine that a second one of the radiofrequency transceiver circuits is associated with a higher quality indication than the first one of the radiofrequency transceiver circuits based on the comparison of the additional quality indications; and
    select the second one of the radiofrequency transceiver circuits in place of the first one of the radiofrequency transceiver circuits for subsequent radiofrequency communication with the implantable medical device as a result of the determination that the second one of the radiofrequency transceiver circuits is associated with a higher quality indication.

3. The communication device of claim 1, wherein the processing circuit is further configured to:
    determine at least one communication parameter used by the first one of the radiofrequency transceiver circuits for the radiofrequency communication with the implantable medical device; and
    send the at least one communication parameter to each of the radiofrequency transceiver circuits that was not selected, wherein the at least one communication parameter is sent to enable each of the non-selected radiofrequency transceiver circuits to monitor radiofrequency communication between the first one of the radiofrequency transceiver circuits and the implantable medical device.

4. The communication device of claim 1, wherein the processing circuit is further configured to:
    identify, for each of the radiofrequency transceiver circuits, an antenna to be used for radiofrequency communication;
    configure each of the radiofrequency transceiver circuits to use a corresponding identified antenna; and
    determine the quality indications based on signals received by the radiofrequency transceiver circuits via the identified antennas.

5. The communication device of claim 1, wherein the radiofrequency communication with the implantable medical device is conducted via a medical implant communication service (MICS) band or an industrial, scientific, and medical (ISM) band.

6. The communication device of claim 1, wherein the radiofrequency communication with the implantable medical device employs a coverage range on the order of 10 meters or less.

7. The communication device of claim 1, wherein the radiofrequency communication with the implantable medical device employs a transmit power on the order of 25 microwatts or less.

8. The communication device of claim 1, wherein the quality indications comprise at least of the group consisting of: received signal strength information corresponding to the radiofrequency signals received by a corresponding one of the radiofrequency transceiver circuits, cyclic redundancy check (CRC) information corresponding to information embedded in the radiofrequency signals received by a corresponding one of the radiofrequency transceiver circuits, error correcting code (ECC) information corresponding to information embedded in the radiofrequency signals received by a corresponding one of the radiofrequency transceiver circuits, and throughput information corresponding to information embedded in the radiofrequency signals received by a corresponding one of the radiofrequency transceiver circuits.

9. The communication device of claim 1, wherein:
    the at least one other radiofrequency transceiver circuit comprises a second radiofrequency transceiver circuit that is embodied in another device that is separate from the communication device; and
    the communication device comprises a third radiofrequency transceiver circuit configured to communicate with the other device via radiofrequency signaling.

10. The communication device of claim 9, wherein the processing circuit is further configured to:
    determine that the communication device is in communication with the other device; and
    communicate with the implantable medical device via the second radiofrequency transceiver circuit and the third radiofrequency transceiver circuit upon selecting the third radiofrequency circuit for the radiofrequency communication with the implantable medical device.

11. The communication device of claim 9, wherein:
    the radiofrequency communication with the implantable medical device is conducted via a medical radiofrequency band; and the radiofrequency signaling is conducted via an IEEE 802.11 radiofrequency band.

12. The communication device of claim 1, wherein the at least one other radiofrequency transceiver circuit is embodied in the communication device.

13. The communication device of claim 1, wherein:
the at least one other radiofrequency transceiver circuit is embodied in another device that is separate from the communication device;
the other device comprises a cable that is coupled to a first connector such that the first connector is electrically coupled with the at least one other radiofrequency transceiver circuit; and
the communication device further comprises a second connector configured to connect to the first connector such that the at least one other radiofrequency transceiver circuit is electrically coupled with the processing circuit.

14. The communication device of claim 1, wherein the communication device is a tablet computing system.

15. The communication device of claim 1, wherein the communication device is a programmer for an implantable cardiac device.

16. A communication device for communicating with an implantable medical device, comprising:
a radiofrequency transceiver circuit configured to receive radiofrequency signals from an implantable medical device; and
a processing circuit configured to:
determine a first quality indication corresponding to reception of the radiofrequency signals by the radiofrequency transceiver circuit;
determine at least one other quality indication corresponding to reception of radiofrequency signals from the implantable medical device by at least one other radiofrequency transceiver circuit;
compare the first quality indication and the at least one other quality indication; and
select a first one of the radiofrequency transceiver circuits for radiofrequency communication with the implantable medical device, wherein the selection is based on the comparison the processing circuit is further configured to send a control signal to each of the non-selected radiofrequency transceiver circuits; and
each control signal sets a corresponding one of the non-selected radiofrequency transceiver circuits to a low power mode.

17. A system for communicating with an implantable medical device, comprising:
a first communication device, comprising
a first radiofrequency transceiver circuit; and
at least one second radiofrequency transceiver circuit configured to communicate via radiofrequency signaling with an implantable medical device; and
a second communication device, comprising:
a third radiofrequency transceiver circuit configured to communicate with the first radiofrequency transceiver circuit;
at least one fourth radiofrequency transceiver circuit configured to communicate via radiofrequency signaling with the implantable medical device; and
a processing circuit configured to select a radiofrequency transceiver circuit for radiofrequency communication with the implantable medical device from a set of radiofrequency transceiver circuits consisting of the at least one second radiofrequency transceiver circuit and the at least one fourth radiofrequency transceiver circuit, wherein the processing circuit is further configured to communicate with the at least one second radiofrequency transceiver circuit via the third radiofrequency transceiver circuit and the first radiofrequency transceiver circuit.

18. The system of claim 17, wherein the selection of the radiofrequency transceiver circuit comprises:
determining, for each radiofrequency transceiver circuit of the set, an indication of communication quality between the implantable medical device and the corresponding radiofrequency transceiver circuit;
comparing the indications; and
selecting the radiofrequency transceiver circuit for the radiofrequency communication based on the comparison.

19. The system of claim 17, wherein:
the at least one second radiofrequency transceiver circuit is embodied in another device that is separate from the first communication device;
the other device comprises a cable that is coupled to a first connector such that the first connector is electrically coupled with the at least one second radiofrequency transceiver circuit; and
the first communication device further comprises a second connector configured to connect to the first connector to enable the communication between the at least one second radiofrequency transceiver circuit and the processing circuit.

20. The system of claim 17, wherein the first communication device further comprises a communication network interface configured to communicate with the processing circuit via the first radiofrequency transceiver circuit and the third radiofrequency transceiver circuit.

21. The system of claim 17, wherein the first communication device further comprises an electrocardiogram circuit configured to communicate with the processing circuit via the first radiofrequency transceiver circuit and the third radiofrequency transceiver circuit.

22. The system of claim 17, wherein:
the first communication device is a base station; and
the second communication device is a tablet computing system.

23. A method for communicating with an implantable medical device, comprising:
determining a first quality indication corresponding to reception of radiofrequency signals from an implantable medical device by a radiofrequency transceiver circuit;
determining at least one other quality indication corresponding to reception of radiofrequency signals from the implantable medical device by at least one other radiofrequency transceiver circuit;
comparing the first quality indication and the at least one other quality indication; and
selecting a first one of the radiofrequency transceiver circuits for radiofrequency communication with the implantable medical device, wherein the selection is based on the comparison.

24. The method of claim 23, further comprising:
determining additional quality indications that correspond to reception of other radiofrequency signals from the implantable medical device by the radiofrequency transceiver circuits;
comparing the additional quality indications;
determining that a second one of the radiofrequency transceiver circuits is associated with a higher quality indication than the first one of the radiofrequency transceiver circuits based on the comparison of the additional quality indications; and selecting the second one of the radiofrequency transceiver circuits in place of the first one of the radiofrequency transceiver circuits for subsequent radiofrequency communication with the implantable medical device as a result of the determination that the second one of the radiofrequency transceiver circuits is associated with a higher quality indication.

25. The method of claim 23, further comprising:

determining at least one communication parameter used by the first one of the radiofrequency transceiver circuits for the radiofrequency communication with the implantable medical device; and sending the at least one communication parameter to each of the radiofrequency transceiver circuits that was not selected, wherein the at least one communication parameter is sent to enable each of the non-selected radiofrequency transceiver circuits to monitor radiofrequency communication between the first one of the radiofrequency transceiver circuits and the implantable medical device.

26. The method of claim 23, further comprising sending a control signal to each of the non-selected radiofrequency transceiver circuits as a result of selecting the first one of the radiofrequency transceiver circuits, wherein each control signal sets a corresponding one of the non-selected radiofrequency transceiver circuits to a low power mode.

27. The method of claim 23, further comprising:

identifying, for each of the radiofrequency transceiver circuits, an antenna to be used for radiofrequency communication;

configuring each of the radiofrequency transceiver circuits to use a corresponding identified antenna; and determining the quality indications based on signals received by the radiofrequency transceiver circuits via the identified antennas.

* * * * *